(12) United States Patent
Frazier et al.

(10) Patent No.: US 7,691,636 B2
(45) Date of Patent: Apr. 6, 2010

(54) METHOD AND APPARATUS FOR COMPENSATING FOR VARIATIONS IN PARTICLE TRAJECTORIES IN ELECTROSTATIC SORTER FOR FLOWCELL CYTOMETER

(75) Inventors: Erich H. Frazier, Fort Lauderdale, FL (US); Todd P. Lary, Homestead, FL (US)

(73) Assignee: Beckman Coulter, Inc., Fullerton, CA (US)

( * ) Notice: Subject to any disclaimer, the term of this patent is extended or adjusted under 35 U.S.C. 154(b) by 0 days.

(21) Appl. No.: 11/752,505

(22) Filed: May 23, 2007

(65) Prior Publication Data

US 2008/0293146 A1 Nov. 27, 2008

(51) Int. Cl.
*G01N 33/48* (2006.01)

(52) U.S. Cl. .......................... 436/63; 436/164; 422/73; 422/82.05; 209/3.2; 209/552; 209/576; 209/127.4; 382/133

(58) Field of Classification Search ....................... None
See application file for complete search history.

(56) References Cited

U.S. PATENT DOCUMENTS

| | | | |
|---|---|---|---|
| 6,079,836 A | 6/2000 | Burr et al. | ...................... 357/70 |
| 6,248,590 B1 * | 6/2001 | Malachowski | ............... 436/63 |
| 6,507,391 B2 * | 1/2003 | Riley et al. | .................... 356/28 |

OTHER PUBLICATIONS

Edwards, Timothy S., Effects of aliasing on numerical integration, available online Sep. 23, 2005, Mechanical systems and signal processing, vol. 21, pp. 165-176.*
Hahn, Karl, Application of integration, 2003, Karl's Calculus Tutor: 12.1 Motion Problems, section 12: Applications of Integration, Retrieved from the internet:<URL:http//www.karlscalculus.org/calc12_0.html>.*
Chung, S. et al,Plastic microchip flow cytometer based on 2-and 3-dimensional hydrodynamic flow focusing, 2003, Microsysem Technologies, vol. 9, p. 525-533.*
Tretheway, Derek C., et al. Apparent fluid slip at hydrophobic microchannel walls, 2002, Physics of Fluids, vol. 14(3), pp. L9-L12.*

* cited by examiner

*Primary Examiner*—Yelena G. Gakh
*Assistant Examiner*—Robert Xu
(74) *Attorney, Agent, or Firm*—Sterne, Kessler, Goldstein & Fox PLLC; Mitchell E. Alter (57) ABSTRACT

A flow cytometer subsystems monitors a particle sensing zone within a fluid transport chamber for the presence of a particle (e.g., blood cell) traveling therethrough, and produces an output pulse, whose width is representative of the trajectory and thereby the length of time that the particle is within the particle sensing zone as it travels through the fluid transport chamber. This output pulse is then processed in accordance with geometry parameters of successive time delay zones of the particle fluid transport chamber through which the particle passes, in order to derive a composite time delay between the sensing of the particle to the time at which a fluid droplet containing the particle will break off from the carrier fluid. The composite time delay is employed to accurately establish the time at which the particle is controllably charged as the particle breaks off from the carrier fluid.

17 Claims, 2 Drawing Sheets

METHOD AND APPARATUS FOR COMPENSATING FOR VARIATIONS IN PARTICLE TRAJECTORIES IN ELECTROSTATIC SORTER FOR FLOWCELL CYTOMETER

FIELD OF THE INVENTION

The present invention relates in general to flow cytometer systems and subsystems thereof, and is particularly directed to a new and improved signal processing and control mechanism therefor, that is operative to monitor a particle sensing zone within a fluid transport chamber for the presence of a particle (e.g., blood cell) traveling therethrough, and to produce an output pulse, whose width is representative of the trajectory and thereby the length of time that the particle is within the particle sensing zone as it travels through the fluid transport chamber. This output pulse is then processed in accordance with geometry parameters of successive time delay zones of the particle fluid transport chamber through which the particle passes, in order to derive a composite time delay between the sensing of the particle to the time at which a fluid droplet containing the particle will break off from the carrier fluid. The composite time delay is employed to accurately establish the time at which the particle is controllably charged as the droplet breaks off from the carrier fluid.

BACKGROUND OF THE INVENTION

Flow cytometers are instruments that are commonly employed in the medical industry to analyze particles (e.g., blood cells) in a patient's body fluid as an adjunct to the diagnosis and treatment of disease. As a non-limiting example, during chemotherapy treatment, such instruments may be used to sort and collect healthy blood cells (stem cells) from a quantity of blood that has been removed from a patient's bone marrow prior to chemotherapy. Once a chemotherapy treatment session is completed, a collected quantity of these cells is the reinjected into the patient, to facilitate migration and healthy blood cell reproduction.

In accordance with the customary operation of a flow cytometer, particles to be analyzed, such as blood cells of a centrifuged blood sample are injected from a storage container into a (pressurized) continuous or uninterrupted stream of carrier fluid (e.g., saline) that travels through a carrier fluid transport chamber in which individual particles are sensed and contained within droplets that break off from the fluid stream exiting the fluid transport chamber. As diagrammatically illustrated in FIG. 1, which shows a portion of a fluid transport chamber 10 of a 'SENSE IN QUARTZ' flow cytometer system, a particle-containing carrier fluid 11 and its surrounding sheath fluid layer 12 are directed along an axial flow direction 13 from a relatively wide diameter portion 14 to a reduced diameter exit orifice 15 of the fluid flow chamber 10.

Figure 1:
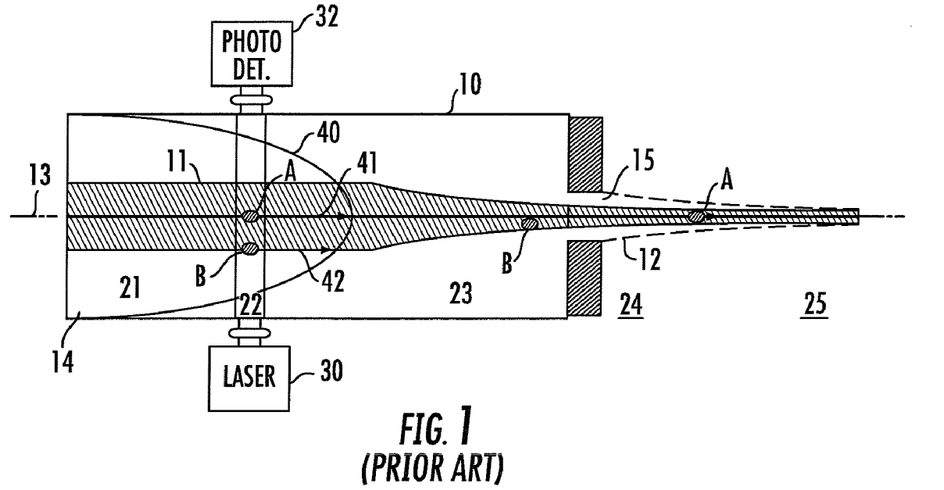
FIG. 1 diagrammatically illustrates a portion of a conventional 'SENSE IN QUARTZ' flow cytometer system.

The particle-carrying fluid 11, that has been introduced into an upstream zone 21 of the chamber, is intersected at a particle-sensing zone 22 by an output (laser) beam 31 emitted by an optical illumination subsystem, such as one or more lasers 30. Located optically in the path of the laser output beam 31 after its being intercepted by the carrier fluid stream are one or more sensors of a photodetector subsystem 32. The photodetecting subsystem is positioned to receive light modulated by the contents of (particles/cells within) the carrier fluid stream, which typically includes light reflected off a cell, the blocking of light by a cell, and a light emission from a fluorescent dye antibody attached to a cell.

Downstream of the particle sensing zone 22 is a fluid stream constriction zone 23, wherein the cross sections of the carrier fluid stream and its surrounding sheath are reduced or constricted, so that the carrier fluid exits the chamber through an exit aperture or orifice 15 at a relatively high velocity relative to its travel within the chamber and enter an air space exit zone 24. From this location the constricted fluid stream, whose cross section is considerably smaller than during its travel through the fluid transport chamber and is sized to accommodate a single particle, continues on through a droplet separation and charging zone 25, where a charge is selectively applied to a droplet as the droplet separates or breaks off the fluid stream 11 proper.

Conventional SENSE IN QUARTZ technology systems of the type shown in FIG. 1 incorporate a fixed time delay period between the time a particle is sensed and analyzed in the sensing zone 22 and the time of the application of a droplet sorting charge in the downstream charging and droplet separation zone 25. The use of a fixed delay constitutes a source of error in the charging/sorting operation due to the fact that not all particles travel at the same effective speed along the transport direction of the fluid, due to the fact that not all particles traverse the same trajectory through the flow chamber.

More particularly, established flow inside a chamber can be generally described as parabolic flow to some degree. In parabolic flow within zone 21 there is a relationship between particles flowing along the central axis relative to those particles traveling closer to a wall of the chamber. These particles will continue at their respective (parabola profile based) velocities unless acted upon by an outside influence. Such an influence is created when the fluid flow is forced through a change in geometry, such as the exit orifice 15. Just upstream of this orifice, there is a constriction of the flow and a subsequent acceleration of the particles relative to the change in cross-sectional area. This acceleration is not uniform and therefore causes a greater acceleration of the particles depending upon wherein the particles are flowing in the fluid stream, thereby separating particles at a faster rate than that occurring in the sensing zone 22 of the chamber. Once the flow exits the area affected by the exit orifice, at zone 24, the velocity can be assumed to be constant, so that there is no further separation of the particles.

Figure 2:
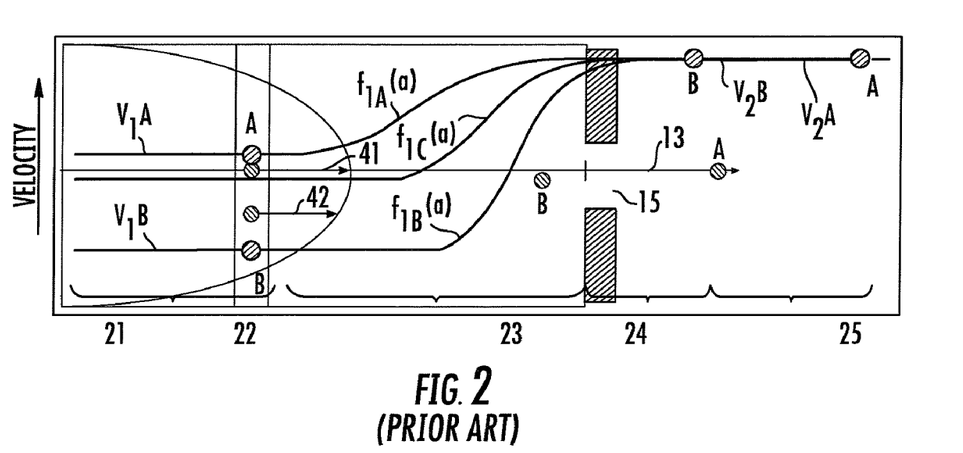
FIG. 2 shows a set of velocity profiles overlaid on the 'SENSE IN QUARTZ' flow cytometer system of FIG. 1.

This differential in velocity and trajectories may be readily understood by referring to FIG. 2, which shows a first particle A traveling along the axis 13 of the carrier fluid channel, and a second particle B that is displaced by some distance from the axis 13 as it travels through the fluid transport chamber. Superimposed on the fluid transport chamber diagram of FIG. 2 is a set of velocity profiles showing three examples of different velocities associated with different positions of particles relative to the fluid transport axis 13. In the illustrated example, within the zone 21, the particle A has a velocity $V_1A$ which is represented by a velocity vector (arrow 41), that coincides with the peak value of a generally parabolic velocity profile of the speed of travel of the carrier fluid through the upstream portion of chamber.

Similarly, within the zone 21, the (off-axis) particle B has a velocity $V_1B$, which is represented by a reduced amplitude velocity vector (arrow 42), which coincides with a reduced value along the velocity profile of the speed of travel of the carrier fluid through the chamber. FIG. 2 also shows within the zone 21 a further (off-axis) velocity $V_1C$ that lies in between associated the velocities $V_1A$ and $V_1B$, and would be associated with an off axis particle (not shown) lying between the coaxial particle A and the off-axis particle B.

From FIG. 2 it is apparent that particles closer to the axis 13 travel at higher velocities as they pass through the sensing zone 22. The velocity profile overlay of FIG. 2 also shows that as the particles leave the sensing zone 22 and approach an acceleration zone 23 adjacent to the exit orifice 15, the speed of the fluid containing the particles must increase in order to comply with the conservation of mass. For the particle A, its velocity increases from a value of $V_1A$ in the sensing zone 22 along a first acceleration profile $f_{1A}$ to the entrance zone 23 to the exit orifice 15. Thereafter, the velocity of particle A increases (accelerates) slightly along a second acceleration profile $f_{2A}(a)$ as its passes through the orifice 15 and travels through the freespace region from zone 24 immediately adjacent to the downstream side of orifice 15 to a downstream zone 25 at a final velocity of $V_2A$. Likewise, the velocity of particle B velocity increases from a value of $V_1B$ at the sensing zone along a first acceleration profile $f_{1B}(a)$, reaching a higher velocity at the entrance zone 23 to the exit orifice 15. Thereafter, the velocity of particle B increases (accelerates) slightly along a second acceleration profile $f_{2B}(a)$ as its passes through the orifice 15 and travels through the freespace region from zone 24 immediately adjacent to the downstream side of orifice 15 to a downstream zone 25 reaching a final velocity of $V_2B$.

From these different velocity profiles it can be seen that the different trajectories of particles A and B cause different arrival times at the point of application of a droplet sorting charge in zone 25, which is downstream of exit orifice 15, so that a fixed time delay will not guarantee that the correct particle will be contained in the sorted droplet. In order to maintain conservation of mass, an off-axis particle, such as the particle B, must undergo a more rapid acceleration than the acceleration of particle A, as it approaches zone 23, so that it will exit the chamber 10 at the speed of the fluid stream. If the two particles A and B are in the sensing zone 22 at the same time, the coaxial particle A, which has the higher velocity, will exit the chamber ahead of the slower particle B, which has to accelerate up to the speed of the fluid stream exiting the chamber at orifice 15. In an attempt to deal with this problem, conventional systems sort more than one droplet; this, in turn, decreases the purity of the sorted populations and increases the dilution of the particles.

SUMMARY OF THE INVENTION

In accordance with the present invention, the drawbacks of using a fixed delay in conventional flow cytometer sorting mechanisms, as described above, are effectively obviated by utilizing the measured velocity of the particle through a sensing zone, together with other analysis parameters, in particular geometry parameters of respectively different zones through the carrier fluid flow chamber, to derive adjusted delays that compensate for the different trajectories of the analyzed particles. As will be described, knowing the relative velocities of the particles allows a calculation to be made of the expected arrival times of particles at the chamber's output/sorting orifice, and the generation of a set of variable delays to control the time of droplet charge. This variable control of the delay period increases the purity of the sorted sample and reduces its dilution. The speed of travel of the particle can be readily measured using one or more laser beams and determining the time between scatter pulses, as a non-limiting example. In addition, time of flight or pulse width can be used as an additional parameter to interject particle size as a factor in the time delay algorithm.

For this purpose, the signal processing system of the present invention comprises a particle sensor such as a photodetector unit, which is operative to generate an output pulse signal that is produced by a particle within the carrier fluid as a result of interaction of that particle and the laser beam illuminating the fluid as it passes through the sensing zone. The pulse signal is coupled to a digital signal processor, which performs a prescribed pulse evaluation routine, including a sort delay calculation, in order to precisely define the time at which a particle-containing drop to be sorted is to be controllably charged by a downstream charging collar, at the point at which the drop of interest breaks off of a stream of droplets that have exited the output orifice of the fluid flow chamber.

The width of the pulse signal is indicative of the velocity of the particle within the fluid flow channel, and provides an initial indication of how close to the axis of the fluid stream the particle is traveling. Where the pulse has a prescribed minimum width, it is inferred that the particle has a trajectory that is coincident with the axis of the fluid stream traveling through and exiting the chamber and is moving at the highest velocity possible through the system. In this instance the time delay between the sensing of the particle and the selective sorting thereof at a location downstream of the exit orifice would be a minimum delay.

However, trajectories of particles within the carrier fluid can be expected to vary, due to the fact that the cross section of the fluid flow path through the chamber varies as one proceeds in an upstream to downstream direction through the fluid flow chamber from the relatively wide upstream zone where the particles enter the chamber to the constriction at the exit orifice. Thus, an off-axis particle, will have a velocity vector that is less than the peak velocity vector of a particle traveling coincident with the axis through the flow chamber, so that the width of the sensor output pulse produced by an off-axis particle will be wider than that produced by a particle that is traveling on the fluid flow axis. Whether the sensed signal is indicative of a particle to be sorted is determined by a signal classification step, which employs one or more prescribed criteria, such as amplitude, to identify pulses associated with particles as opposed to those associated with noise. Where a particle-representative pulse has been detected, a sort delay calculation step is executed. The pulse width determination information is measured and applied to the sort delay calculation. The output of the sort delay calculation step is a time delay value that will be used to control the time at which a charge is applied to a droplet charging collar thereby charging the droplet containing the particle of interest.

In accordance with the present invention, the sort delay calculation is comprised of a plurality of components that are respectively associated with different zones of the flow chamber through which the particle of interest passes. The first zone is the particle sensing zone in which the particle is sensed, as by way of a laser illumination subsystem. The output pulse produced by the particle sensor has rising and falling edges that define the width of the pulse associated with a potential particle of interest. The particle-sensing zone is upstream of two fluid-constricting zones of the fluid flow chamber, so that the particle of interest has some constant velocity in sensing zone.

For a particle traveling coincident with the axis of fluid flow, the constant velocity is defined at the peak of the velocity profile through the flow chamber. Within the sort time delay calculation, the first component to be determined is the time its takes the particle to transit the width of the particle sensing zone.

A second time delay component is the time delay associated with the travel of the particle from the constant velocity sensing zone through a first acceleration zone leading to the exit orifice. Because there is a constriction of the carrier fluid in this zone, the particle will undergo an acceleration as it approaches the exit orifice. Therefore, the time required for the particle to traverse this distance is equal to the distance divided by the velocity over that distance. Because the particle is undergoing an acceleration in this region the velocity is not constant, and it is necessary to integrate the acceleration function between the zone boundaries at the downstream end of the particle sensing zone and the distance therefrom to the exit orifice. The acceleration function may be determined empirically or deterministically based upon the geometry parameters of the fluid flow system. There is an additional acceleration of the particle through the exit orifice and an associated transit time therefor is calculated.

Once the particle has exited the orifice, it is traveling at a constant exit velocity along the axis of the fluid stream. The distance from the exit orifice to the droplet charging location divided by this velocity is the final time component of the composite time delay. In other words, for an arbitrary particle A, a composite time delay $T_dA$ may be defined as:

$$T_dA = D_2/V_1A + D_3 \bigg/ \int_{D_2}^{D_3} f_{1A}(a)da + D_4 \bigg/ \int_{D_3}^{D_4} f_{2A}(a)da + D_5/V_2A$$

It will thus be appreciated, that from the instant a particle is initially sensed until the particle arrives at the break-off, charging location downstream of the exit orifice, there is a composite delay time $T_d$ equal to the sum of the incremental delay components described. This composite delay time is used to delay the application of a control signal to a droplet charge amplifier the output of which is coupled to an electrostatic charging collar surrounding the travel path of the droplet sequence. The charging collar is positioned vertically downstream of the fluid chamber exit orifice and upstream of an associated set of electrostatic (opposite polarity, high voltage) deflection plates between which the stream of charged droplets pass as they travel downwardly and are either sorted along a sort path into a sorted droplet collection container, or allowed to pass unsorted along a separate travel path into an aborted or discarded waste container.

Advantageously, the charging mechanism of the present invention is dynamic, as it adapts to where within the fluid stream in the fluid flow chamber the particles to be sorted are located. This serves to increase the purity of the sorted sample and reduces its dilution. The speed of travel of the particle can be readily measured using one or more laser beams and determining the time between scatter pulses. In addition, time of flight or pulse width can be used as an additional parameter to interject particle size as a factor in the time delay calculation.

DETAILED DESCRIPTION

Before detailing the architecture and methodology for compensating for variations in particle trajectories in a flow-cell cytometer having an electrostatic sorter in accordance with the present invention, it should be observed that the invention resides primarily in a prescribed novel arrangement of conventional analog and digital circuits and components. Consequently, the configurations of such circuits and components and the manner in which they may be interfaced with a cytometer fluid flow chamber and an associated particle droplet charging unit have, for the most part, been shown in the drawings by readily understandable schematic block diagrams, which show only those specific aspects that are pertinent to the present invention, so as not to obscure the disclosure with details which will be readily apparent to those skilled in the art having the benefit of the description herein. Thus, the schematic block diagrams are primarily intended to show the major components of various embodiments of the invention in convenient functional groupings, whereby the present invention may be more readily understood.

Figure 3:
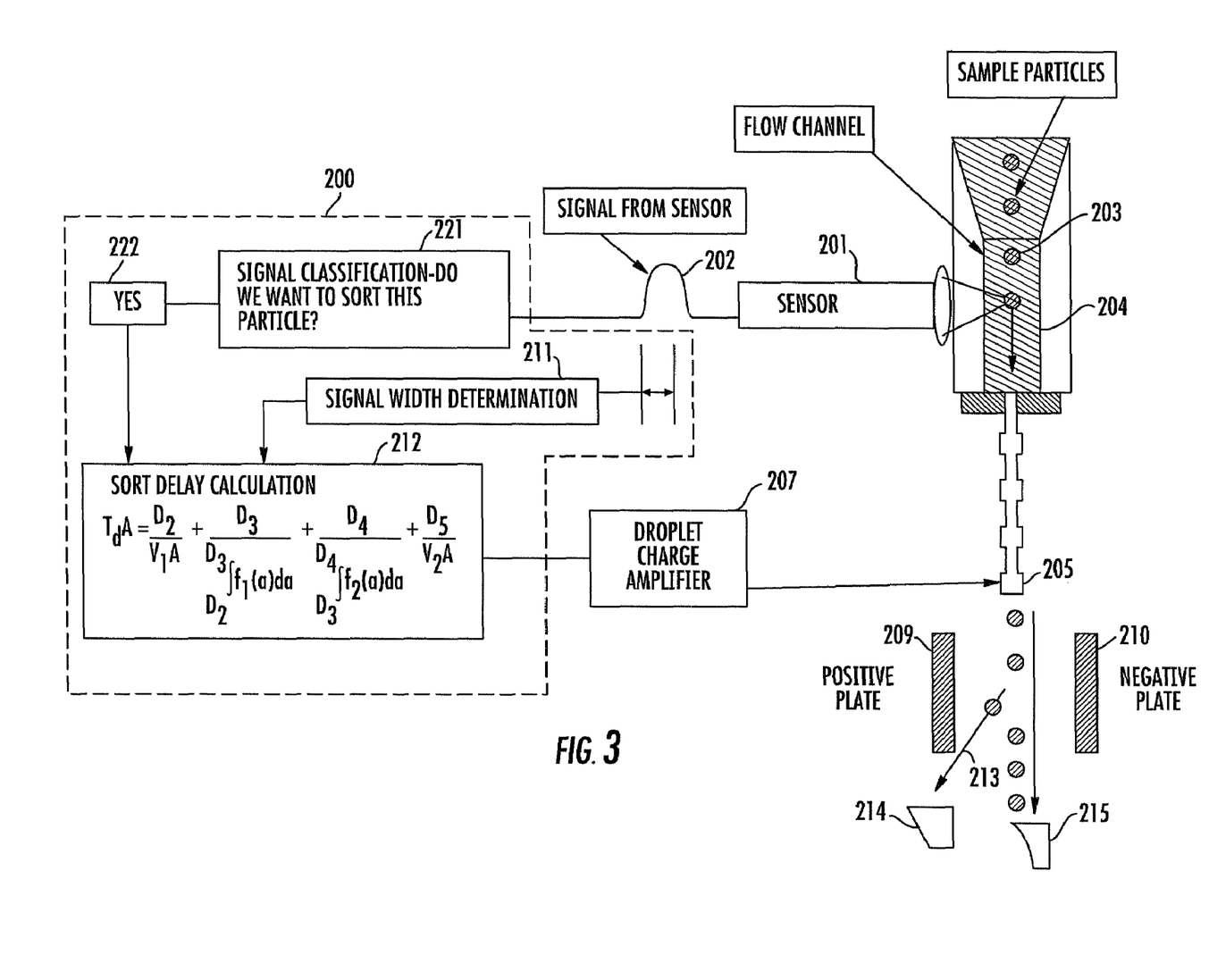
FIG. 3 diagrammatically illustrates an embodiment of the signal processing system of the present invention and the manner in which it may be readily interfaced with a conventional flow cytometer fluid flow chamber of the type described with reference to FIGS. 1 and 2.

Attention is now directed to FIG. 3, wherein an embodiment of the signal processing system of the present invention and the manner in which it is interfaced with a conventional flow cytometer fluid flow chamber of the type described with reference to FIGS. 1 and 2 is diagrammatically illustrated. As shown therein, the system comprises a sensor 201, such as a photodetector unit, which is operative to generate an output pulse signal 202 that is produced by a particle 203 within the carrier fluid 204 as a result of interaction of that particle and the laser beam illuminating the sensing zone 22. The pulse is coupled to a digital signal processor 200, which performs a prescribed pulse evaluation routine, including a sort delay calculation, in order to precisely define the time at which a particle-containing drop to be sorted is to be controllably charged by a downstream charging collar, at the point at which the drop of interest breaks off of a stream of droplets that have exited the output orifice 206 of the fluid flow chamber.

The width of the pulse signal 202 is indicative of the velocity of the particle within the fluid flow channel, and provides an initial indication of how close to the axis of the fluid stream the particle is traveling. Where the pulse has a prescribed minimum width, which can be determined experimentally or deterministically, it is inferred that the particle has a trajectory that is coincident with the axis of the fluid stream traveling through and exiting the chamber (which would correspond to the particle A, described above), and is therefore moving at the highest velocity possible through the system. In this instance the time delay $T_dA$ between the sensing of the particle and the selective sorting thereof at a location 205 downstream of the exit orifice 206 would be a minimum delay.

As described above, however, the trajectories of particles contained within the carrier fluid can be expected to vary, due to the fact that the cross section of the fluid flow path through the chamber 10 varies as one proceeds in an upstream to downstream direction through the fluid flow chamber from the relatively wide upstream zone 21 where the particles enter the chamber to the constriction at the exit orifice 15. As pointed out above, and as shown in FIG. 2, an off-axis particle, such as particle B, has a velocity vector (42) which is less than the peak velocity vector 41 of a particle A along the axis through the flow chamber 13, so that the width of the sensor output pulse produced by particle B will be wider than that produced by particle A. Whether the sensed signal is indicative of a particle to be sorted is determined by a signal classification step 221. If the answer to this step is YES as shown at 222, a sort delay calculation step 212 is executed, as will be described. The pulse width determination information is measured at 211 and applied to the sort delay calculation 212. The output of the sort delay calculation step is a time delay value that will be used to control the time at which a charge is applied to a droplet charging collar thereby charging the droplet containing the particle of interest.

In accordance with the present invention, the sort delay calculation is comprised of a plurality of components that are respectively associated with different zones of the flow chamber through which the particle of interest passes. The first zone is the sensing zone 22 at which the particle is sensed by the laser illumination subsystem 30. The output pulse of the sensor 201 produces rising and falling edges that define the width of the pulse associated with a potential particle of interest. Sensing zone 22 is upstream of the two fluid-constricting zones 23 and 24 of the fluid flow chamber, so that the particle of interest has some constant velocity at zone 22. For the particle A, the constant velocity is $V_1A$ (represented by arrow 42 in FIG. 1) and is defined at the peak of the (parabolic) velocity profile 40. Within the sort time delay calculation, the first component to be determined is the time its takes the particle to transit the distance D2, which corresponds to the distance (D) of travel through the sensing zone 22. This delay component for particle A is denoted as time delay $T_{d2}A$.

A second time delay component is the time delay associated with the travel of the particle from the sensing zone 22 to a first acceleration zone 23. The associated distance is denoted as distance D3. Because there is a constriction of the carrier fluid in this region, the particle A will undergo an acceleration $f_{1A}(a)$ as it approaches the exit orifice 15. Therefore, the time $T_{d23}A$ required for the particle A to traverse the distance D3 is equal to the distance D3 divided by the velocity over that distance. Because the particle A is undergoing an acceleration in this region the velocity is not constant, and it is necessary to integrate the acceleration function $f_{1A}(a)$ between the zone boundaries at the downstream end of distance D2 and the distance D3. The acceleration function $f_{1A}(a)$ may be determined empirically or deterministically based upon the geometry parameters of the fluid flow system.

As a non-limiting example, where the acceleration zone is a uniform symmetric reduction of the cross-sectional area of the flow, the acceleration function would be a constant (k) that can be determined empirically or using numerical fluid flow simulation calculations. In this case:

$f_{1A} = k$

In general, the time $T_{d23}A$ required for the particle A to traverse the distance between zones 22 and 23 is definable as:

$$T_{d23}A = D_3 \Big/ \int_{D_2}^{D_3} f_{1A}(a)da$$

Similarly, the time $T_{d34}A$ required for the particle A to traverse the length of the orifice between zones 23 and 24 is definable as:

$$T_{d34}A = D_4 \Big/ \int_{D_3}^{D_4} f_{2A}(a)da$$

As a non-limiting example, where the acceleration zone is a uniform symmetric reduction of the cross-sectional area of the flow, the acceleration function would be a constant (k) that can be determined empirically or using numerical fluid flow simulation calculations. In this case:

$f_{2A} = k$

Once the particle has exited the orifice 15, it is traveling at a constant exit velocity $V_2A$ along the axis of the fluid stream. The distance D5 from the exit orifice to the droplet charging location divided by this velocity is the time $T_{45}A$ required for the particle to travel the distance D5.

It can be seen, therefore, from the instant that the particle A was initially sensed by sensor 201 until the particle arrives at location 205 downstream of the exit orifice 206, a composite delay time $T_dA$ equal to the sum of the incremental delay components described above has elapsed. This composite delay time is used to delay the application of a control signal to a droplet charge amplifier 207, the output of which is coupled to an electrostatic charging collar 208 surrounding the travel path of the droplet sequence. Charging collar 208 may comprise a metallic cylinder that is located so as to surround the location along the droplet sequence travel path where the individual droplets separate from the fluid stream, and is typically several droplets in length. The charging collar is positioned vertically downstream of the fluid chamber exit orifice 206 and upstream of an associated set of electrostatic (opposite polarity, high voltage) deflection plates 209 and 210, between which the stream of charged droplets pass as they travel downwardly and are either sorted along a sort path 213 into a sorted droplet collection container 214, or allowed to pass unsorted along a separate travel path into an aborted or discarded waste container 215.

In other words, for particle A, a composite time delay $T_dA$ may be defined as:

$$T_dA = D_2/V_1A + D_3 \Big/ \int_{D_2}^{D_3} f_{1A}(a)da + D_4 \Big/ \int_{D_3}^{D_4} f_{2A}(a)da + D_5/V_2A$$

Likewise, for the case of particle B, which has an initially lower velocity than particle A, from the instant that the particle B is sensed by sensor 201 until particle B arrives at location 205 downstream of the exit orifice 206, a composite delay time $T_dB$ equal to the sum of the incremental delay components described above has elapsed. For particle B, a composite time delay $T_dB$ may be defined as:

$$T_dB = D_2/V_1B + D_3 \Big/ \int_{D_2}^{D_3} f_{1B}(a)da + D_4 \Big/ \int_{D_3}^{D_4} f_{2B}(a)da + D_5/V_2B$$

From the velocity profiles of FIG. 2, it can be seen that particle A is accelerated to its maximum velocity through the output orifice well in advance of the time it takes for particle B to be accelerated to its maximum velocity through the output orifice. Consequently, the composite delay for particle A from the time it is sensed in the sensing zone 22 until it is charged by the charging collar 208 will be shorter than the composite delay for particle B. It will be appreciated, therefore, that the charging mechanism of the present invention is dynamic, as it adapts to where within the fluid stream in the fluid flow chamber the particles to be sorted are located. As pointed out above, this serves to increase the purity of the sorted sample and reduces its dilution. The speed of travel of the particle can be readily measured using one or more laser beams and determining the time between scatter pulses. In addition, time of flight or pulse width can be used as an additional parameter to interject particle size as a factor in the time delay calculation.

While I have shown and described an embodiment in accordance with the present invention, it is to be understood that the same is not limited thereto but is susceptible to numerous changes and modifications as known to a person skilled in the art, and I therefore do not wish to be limited to the details shown and described herein, but intend to cover all such changes and modifications as are obvious to one of ordinary skill in the art.

What is claimed:

1. For use with a flow cytometer, a method of controlling the point at which droplets are controllably charged and break off from a carrier fluid containing particles to be sorted, said method comprising the steps of:
   (a) monitoring a prescribed zone within a particle fluid transport chamber having a change in cross-sectional width along the length thereof for the presence of a particle traveling therethrough, and producing an output pulse having a width that is representative of the length of time that said particle is within said prescribed zone as it travels through said particle fluid transport chamber;
   (b) calculating a composite time delay for the particle based on the change in cross-sectional width of said particle fluid transport chamber and the position of said particle relative to the axis of a stream of the carrier fluid, between the time that said particle is sensed in step (a) as being present in said prescribed zone and the time at which a droplet containing said particle will break off from said carrier fluid; and
   (c) using said composite time delay calculated in step (b) to controllably charge said particle as said particle breaks off from said carrier fluid.

2. The method according to claim 1, wherein step (b) comprises calculating said composite time delay in accordance with changes in the cross-sectional widths of successive zones of said particle fluid transport chamber through which carrier fluid containing said particle passes.

3. The method according to claim 2, wherein step (b) comprises calculating said composite time delay as a sum of respective time delays associated with changes in the cross-sectional widths of said successive zones of said particle fluid transport chamber through which carrier fluid containing said particle passes.

4. The method according to claim 2, wherein particles within said carrier fluid undergo acceleration in the course of their travel though at least one of said successive zones of said particle fluid transport chamber through which carrier fluid containing said particle passes.

5. The method according to claim 4, wherein step (b) comprises calculating a respective time delay component of said composite time delay for a zone of said particle fluid transport chamber in which said carrier fluid undergoes acceleration by performing integration of an acceleration function between opposite ends of said zone.

6. The method according to claim 1, wherein step (b) comprises calculating composite time delay of an arbitrary particle A contained in said carrier fluid in accordance with the expression:

$$T_d A = D_2/V_1 A + D_3 \bigg/ \int_{D_2}^{D_3} f_{1A}(a) da + D_4 \bigg/ \int_{D_3}^{D_4} f_{2A}(a) da + D_5/V_2 A$$

where:
$T_d A$ is the composite time delay,
$D_2$ is the distance through said prescribed zone,
$V_1 A$ is the velocity of said particle though said prescribed zone;
$D_3$ is the distance between said prescribed zone and a zone adjacent to said output orifice;

$$\int_{D_2}^{D_3} f_{1a}(a) da$$

is the velocity of the particle A between said prescribed zone and said zone adjacent to said output orifice;
$D_4$ is the distance through said output orifice between said zone adjacent to said output orifice and a location downstream of said output orifice, $$\int_{D_3}^{D_4} f_{2a}(a) da$$

is the velocity of the particle A through said output orifice,
$D_5$ is the distance from said location downstream of said output orifice to a location where a drop containing said particle A is charged and separated from said carrier fluid, and
$V_2 A$ is the velocity of said particle downstream of said output orifice.

7. For use with a flow cytometer, a cytometer subsystem for controlling the point at which droplets are controllably charged and break off from a carrier fluid containing particles to be sorted, said subsystem comprising:
   a particle sensor which is operative to monitor a prescribed zone within a particle fluid transport chamber having a change in cross-sectional width along the length thereof for the presence of a particle traveling therethrough, and to produce an output pulse having a width that is representative of the length of time that said particle is within said prescribed zone as it travels through said particle fluid transport chamber;
   a signal processor, which is coupled to receive said output pulse from said particle sensor, and is operative to calculate a composite time delay based on the change in cross-sectional width of said particle fluid transport chamber and the position of said particle relative to the axis of a stream of the carrier fluid, between the time that said particle is sensed as being present in said prescribed zone and the time at which a droplet containing said particle will break off from said carrier fluid; and
   a droplet charger that is operative to controllably charge a droplet containing said particle at the termination of said composite time delay as calculated by said signal processor.

8. The cytometer subsystem according to claim 7, wherein said signal processor is operative to calculate said composite time delay in accordance with changes in the cross-sectional widths of successive zones of said particle fluid transport chamber through which carrier fluid containing said particle passes.

9. The cytometer subsystem according to claim 8, wherein said signal processor is operative to calculate said composite time delay as a sum of respective time delays associated with changes in the cross-sectional widths of said successive zones of said particle fluid transport chamber through which carrier fluid containing said particle passes.

10. The cytometer subsystem according to claim 8, wherein particles within said carrier fluid undergo acceleration in the course of their travel through at least one of said successive zones of said particle fluid transport chamber through which carrier fluid containing said particle passes.

11. The cytometer subsystem according to claim 10, wherein said signal processor is operative to calculate a respective time delay component of said composite time delay for a zone of said particle fluid transport chamber in which said carrier fluid undergoes acceleration by performing integration of an acceleration function between opposite ends of said zone.

12. The cytometer subsystem according to claim 7, wherein said signal processor is operative to calculate the composite time delay of an arbitrary particle A contained in said carrier fluid in accordance with the expression:

$$T_d A = D_2/V_1 A + D_3 \int_{D_2}^{D_3} f_{1A}(a)da + D_4 \Big/ \int_{D_3}^{D_4} f_{2A}(a)da + D_5/V_2 A$$

where:
$T_d A$ is the composite time delay,
$D_2$ is the distance through said prescribed zone,
$V_1 A$ is the velocity of said particle through said prescribed zone;
$D_3$ is the distance between said prescribed zone and a zone adjacent to said output orifice;

$$\int_{D_2}^{D_3} f_{1a}(a)da$$

is the velocity of the particle A between said prescribed zone and said zone adjacent to said output orifice;
$D_4$ is the distance through said output orifice between said zone adjacent to said output orifice and a location downstream of said output orifice,
is the velocity of the particle A through said output orifice, $$\int_{D_3}^{D_4} f_{2a}(a)da$$

$D_5$ is the distance from said location downstream of said output orifice to a location where a drop containing said particle A is charged and separated from said cater fluid, and
$V_2 A$ is the velocity of said particle downstream of said output orifice.

13. For use with a flow cytometer, a method of controlling the point at which droplets are controllably charged and break off from a cater fluid containing particles to be sorted, said method comprising the steps of:
(a) calculating travel times of a particle to be sorted through successive zones of a particle fluid transport chamber through which said particle travels in the course of its transit to the point at which a droplet containing said particle is to be charged and break off from said cater fluid, said calculating including monitoring a prescribed zone within the particle fluid transport chamber, determining the position of said particle in a stream of said cater fluid passing through the zone compared to the axis of the stream, and calculating time delay for a particle in that zone based on an acceleration profile for the particle determined from the position of the particle compared to the axis of the stream;

(b) calculating a composite time delay for said particle in accordance with said travel times calculated in step (a); and
(c) using said composite time delay calculated in step (b) to controllably charge said particle as said particle breaks off from said cater fluid.

14. The method according to claim 13, wherein step (a) comprises calculating said travel times in accordance with changes in cross-sectional widths of successive zones of said particle fluid transport chamber through which carrier fluid containing said particle passes.

15. The method according to claim 14, wherein particles within said carrier fluid undergo acceleration in the course of their travel through at least one of said successive zones of said particle fluid transport chamber through which carrier fluid containing said particle passes.

16. The method according to claim 15, wherein step (a) comprises calculating a respective time delay component of said composite time delay for a zone of said particle fluid transport chamber in which said carrier fluid undergoes acceleration by performing integration of an acceleration function between opposite ends of said zone.

17. The method according to claim 7, wherein step (b) comprises calculating the composite time delay of an arbitrary particle A contained in said carrier fluid in accordance with the expression:
where:

$$T_d A = D_2/V_1 A + D_3 \int_{D_2}^{D_3} f_{1A}(a)da + D_4 \Big/ \int_{D_3}^{D_4} f_{2A}(a)da + D_5/V_2 A$$

$T_d A$ is the composite time delay,
$D_2$ is the distance through said prescribed zone,
$V_1 A$ is the velocity of said particle through said prescribed zone;
$D_3$ is the distance between said prescribed zone and a zone adjacent to said output orifice;

$$\int_{D_2}^{D_3} f_{1a}(a)da$$

is the velocity of the particle A between said prescribed zone and said zone adjacent to said output orifice;
$D_4$ is the distance through said output orifice between said zone adjacent to said output orifice and a location downstream of said output orifice,
is the velocity of the particle A through said output orifice, $$\int_{D_3}^{D_4} f_{2a}(a)da$$

$D_5$ is the distance from said location downstream of said output orifice to a location where a drop containing said particle A is charged and separated from said carrier fluid, and
$V_2 A$ is the velocity of said particle downstream of said output orifice.

* * * * *

UNITED STATES PATENT AND TRADEMARK OFFICE
CERTIFICATE OF CORRECTION

PATENT NO.        : 7,691,636 B2
APPLICATION NO.   : 11/752505
DATED             : April 6, 2010
INVENTOR(S)       : Erich H. Frazier and Todd P. Lary It is certified that error appears in the above-identified patent and that said Letters Patent is hereby corrected as shown below:

Title Page, Item 57, line 1, "subsystems" should read --subsystem--
Column 1, line 40, "is the reinjected" should read --is then reinjected--
Column 2, line 6, "enter" should read --enters--
Column 2, line 37, "wherein" should read --where--
Column 2, line 63, "associated the" should read --the associated--
Column 3, line 7, "acceleration profile f1A to" should read --acceleration profile f1A(a) from--
Column 3, line 10, "as its passes" should read --as it passes--
Column 3, line 14, "particle B velocity increases" should read --particle B increases--
Column 4, line 28, "particle," should read --particle--
Column 4, line 61, "its takes" should read --it takes--
Column 6, line 59, "axis through the flow chamber 13" should read --axis 13 through the flow chamber 10--
Column 7, line 16, "arrow 42" should read --arrow 41--
Column 7, line 18, "its takes" should read --it takes--
Column 8, line 4, "$T_{45}A$" should read --$T_{d45}A$--

Column 10, line 5, " $\int_{D_2}^{D_3} f_{1a}(a)da$ " should read -- $\int_{D_2}^{D_3} f_{1A}(a)da$ --

Column 10, line 17, " $\int_{D_3}^{D_4} f_{2a}(a)da$ " should read -- $\int_{D_3}^{D_4} f_{2A}(a)da$ --

Column 11, line 15,

" $T_d A = D_2/V_1 A + D_3 \int_{D_2}^{D_3} f_{1A}(a)da + D_4/\int_{D_3}^{D_4} f_{2A}(a)da + D_5/V_2 A$ "

Signed and Sealed this
Twenty-ninth Day of January, 2013

David J. Kappos
*Director of the United States Patent and Trademark Office*

CERTIFICATE OF CORRECTION (continued)
U.S. Pat. No. 7,691,636 B2 should read $$T_d A = D_2/V_1 A + D_3/\int_{D_2}^{D_3} f_{1A}(a)da + D_4/\int_{D_3}^{D_4} f_{2A}(a)da + D_5/V_2 A$$

--  --

Column 11, line 30, " $\int_{D_2}^{D_3} f_{1a}(a)da$ " should read -- $\int_{D_2}^{D_3} f_{1A}(a)da$ --

Column 11, lines 39-40,
"is the velocity of the particle A through said output orifice, $$\int_{D_3}^{D_4} f_{2a}(a)da$$

"

should read $$\int_{D_3}^{D_4} f_{2A}(a)da$$

-- is the velocity of the particle A through said output orifice,--

Column 12, line 30,

" $$T_d A = D_2/V_1 A + D_3\int_{D_2}^{D_3} f_{1A}(a)da + D_4/\int_{D_3}^{D_4} f_{2A}(a)da + D_5/V_2 A$$ "

should read $$T_d A = D_2/V_1 A + D_3/\int_{D_2}^{D_3} f_{1A}(a)da + D_4/\int_{D_3}^{D_4} f_{2A}(a)da + D_5/V_2 A$$

-- --

Column 12, line 45, " $\int_{D_2}^{D_3} f_{1a}(a)da$ " should read -- $\int_{D_2}^{D_3} f_{1A}(a)da$ --

Column 12, lines 54-55,
"is the velocity of the particle A through said output orifice, $$\int_{D_3}^{D_4} f_{2a}(a)da$$

"

should read $$\int_{D_3}^{D_4} f_{2A}(a)da$$

is the velocity of the particle A through said output orifice,--